United States Patent
Hoof

(10) Patent No.: US 8,540,734 B2
(45) Date of Patent: Sep. 24, 2013

(54) SUTURE MANAGEMENT AND TENSIONING DEVICES AND METHODS FOR SOFT TISSUE RECONSTRUCTION OR BONE-TO-BONE FIXATION

(75) Inventor: Jordan A. Hoof, Phoenix, AZ (US)

(73) Assignee: Cayenne Medical, Inc., Scottsdale, AZ (US)

( * ) Notice: Subject to any disclaimer, the term of this patent is extended or adjusted under 35 U.S.C. 154(b) by 639 days.

(21) Appl. No.: 11/943,566

(22) Filed: Nov. 20, 2007

(65) Prior Publication Data

US 2008/0154260 A1 Jun. 26, 2008

Related U.S. Application Data

(60) Provisional application No. 60/860,533, filed on Nov. 21, 2006.

(51) Int. Cl.
*A61B 17/04* (2006.01)

(52) U.S. Cl.
USPC ............................................ 606/144; 606/148

(58) Field of Classification Search
USPC .................. 606/232, 139, 144–148, 74, 103, 606/86 R, 99, 102; 73/1.08, 1.15, 862.381, 73/862.391, 862.392, 862.393; 289/17; 112/169; 600/587
See application file for complete search history.

(56) References Cited

U.S. PATENT DOCUMENTS

| | | | |
|---|---|---|---|
| 3,507,270 A * | 4/1970 | Ferrier | 600/481 |
| 3,931,821 A * | 1/1976 | Kletschka et al. | 606/233 |
| 4,950,271 A * | 8/1990 | Lewis et al. | 606/102 |
| 4,957,498 A | 9/1990 | Caspari et al. | |
| 5,085,661 A | 2/1992 | Moss | |
| 5,188,636 A | 2/1993 | Fedotov | |
| 5,281,237 A | 1/1994 | Gimpelson | |
| RE34,762 E * | 10/1994 | Goble et al. | 606/96 |
| 5,431,666 A | 7/1995 | Sauer et al. | |
| 5,439,467 A | 8/1995 | Benderev et al. | |
| 5,507,750 A | 4/1996 | Goble et al. | |
| 5,707,395 A * | 1/1998 | Li | 606/232 |
| 5,713,897 A * | 2/1998 | Goble et al. | 606/53 |
| 5,788,697 A * | 8/1998 | Kilpela et al. | 606/74 |
| 5,810,848 A * | 9/1998 | Hayhurst | 606/144 |
| 5,846,254 A | 12/1998 | Schulze et al. | |
| 5,980,473 A * | 11/1999 | Korakianitis et al. | 600/587 |
| 6,015,428 A * | 1/2000 | Pagedas | 606/232 |
| 6,171,310 B1 * | 1/2001 | Giordano et al. | 606/60 |
| 6,533,795 B1 | 3/2003 | Tran et al. | |

(Continued)

OTHER PUBLICATIONS

International Search Report, Jun. 25, 2008, corresponding to PCT Application No. PCT/US07/85317; Written Opinion of the International Searching Authority, Jun. 25, 2008, corresponding to PCT Application No. PCT/US07/85317.

*Primary Examiner* — Corrine M McDermott
*Assistant Examiner* — Mark Mashack
(74) *Attorney, Agent, or Firm* — Stout, Uxa, Buyan & Mullins, LLP; Donald E. Stout

(57) ABSTRACT

An adjustable, stand-alone tensioning system requires no additional fixturing, weights, or bone surface modification, and allows a single practitioner to provide an adjustable and repeatable tension to a soft tissue graft, and to install the final fixation implant. Its design facilitates introduction of the suture component of the graft into the tensioning process by simplifying retention of the suture. An even, regulated and reproducible tension is easily achieved without requiring the practitioner to manually pull on the suture strands to maintain graft tension.

4 Claims, 7 Drawing Sheets

(56) References Cited

U.S. PATENT DOCUMENTS

| | | | |
|---|---|---|---|
| 6,547,778 B1 * | 4/2003 | Sklar et al. ........................ 606/1 |
| 6,551,330 B1 | 4/2003 | Bain et al. |
| 6,761,722 B2 * | 7/2004 | Cole et al. ........................ 606/74 |
| 6,770,084 B1 | 8/2004 | Bain et al. |
| 7,371,244 B2 * | 5/2008 | Chatlynne et al. ............ 606/148 |
| 7,442,172 B2 * | 10/2008 | Kirkpatrick et al. ........... 600/595 |
| 7,678,135 B2 * | 3/2010 | Maahs et al. ................... 606/232 |
| 7,686,810 B2 * | 3/2010 | West et al. ....................... 606/88 |
| 7,887,564 B2 * | 2/2011 | Boehringer et al. ........... 606/232 |
| 2002/0091391 A1 * | 7/2002 | Cole et al. ........................ 606/72 |
| 2002/0120280 A1 | 8/2002 | Wotton, III |
| 2003/0176920 A1 * | 9/2003 | Sklar et al. ................... 623/13.13 |
| 2003/0208210 A1 * | 11/2003 | Dreyfuss et al. .............. 606/144 |
| 2004/0068267 A1 | 4/2004 | Harvie et al. |
| 2004/0098050 A1 | 5/2004 | Foerster et al. |
| 2004/0122456 A1 * | 6/2004 | Saadat et al. ................... 606/157 |
| 2005/0027226 A1 | 2/2005 | Stutz et al. |
| 2005/0049597 A1 * | 3/2005 | West et al. ....................... 606/72 |

\* cited by examiner

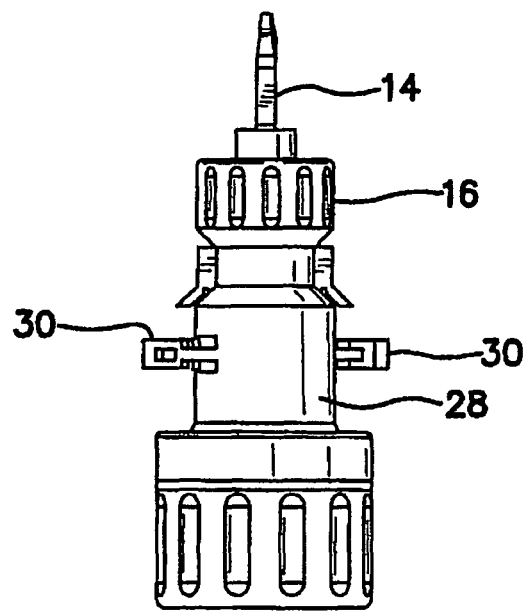
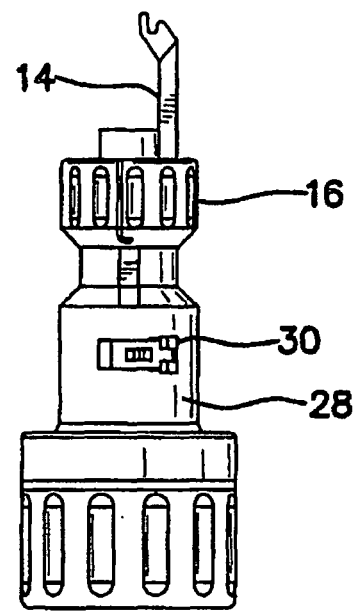
FIG. 3A  FIG. 3B
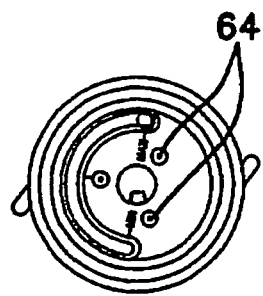
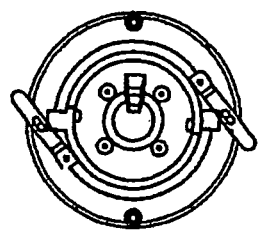
FIG. 3C  FIG. 3D

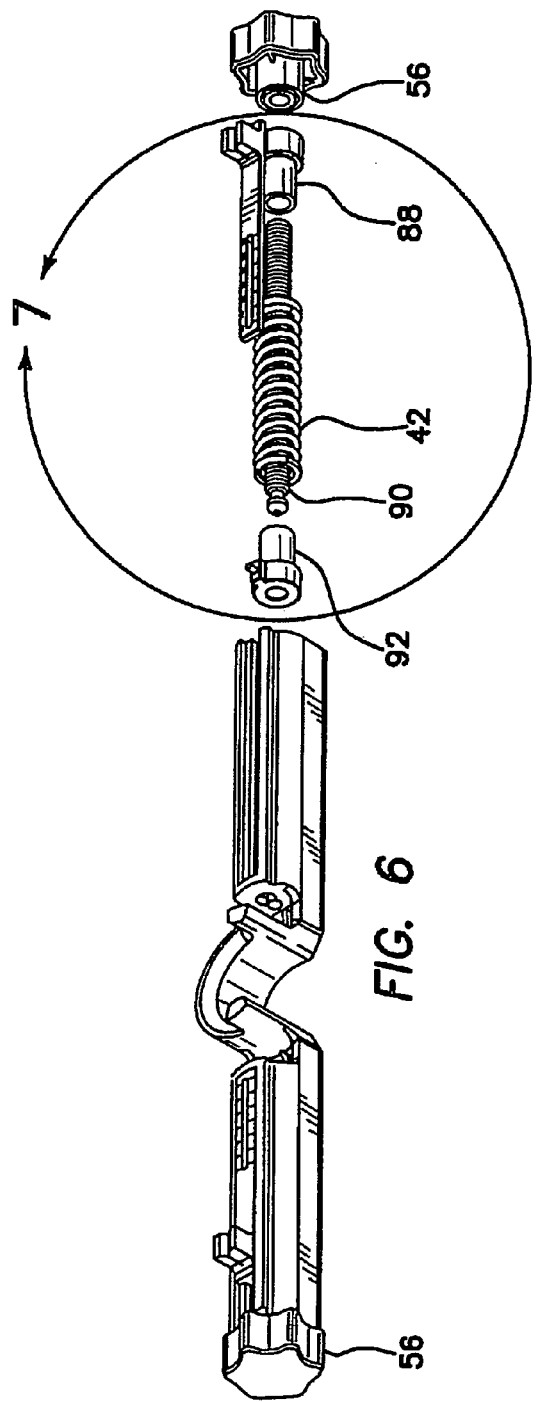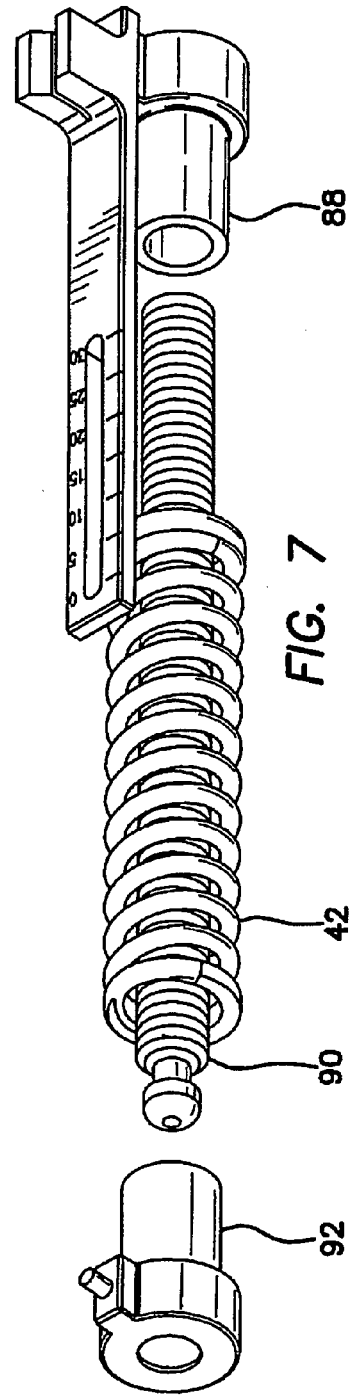

SUTURE MANAGEMENT AND TENSIONING DEVICES AND METHODS FOR SOFT TISSUE RECONSTRUCTION OR BONE-TO-BONE FIXATION

This application claims the benefit under 35 U.S.C. 119(e) of the filing date of Provisional U.S. Application Ser. No. 60/860,533, entitled Suture Management and Tensioning Device for Soft Tissue Reconstruction or Bone-to-Bone Fixation, filed on Nov. 21, 2006, which application is expressly and entirely incorporated herein by reference.

BACKGROUND OF THE INVENTION

The present invention relates generally to devices, systems and methods for material fixation, and, more particularly, to suture management and tensioning devices used during soft tissue reconstruction or bone-to-bone fixation that will assist in the repair of many soft tissue injuries, such as in the reconstruction of the Anterior Cruciate Ligament (ACL).

Prior to completing the final steps of fixation during an ACL repair, the reconstructed ligament must be tensioned in order to establish joint stability. Current devices used to establish ligament pretension require the practitioner to apply and maintain a manual tensile force of the graft during tibial fixation. Devices relying on this technique have proven to be cumbersome, and oftentimes require time consuming steps to prepare the suture component of the tensioning process. These devices also require unnecessary physical exertion, and often require an additional assistant during the final phases of graft fixation. Still other ligament tensioning devices require external fixturing and/or modification of the bone surface to support the tensioning process.

Studies have shown that the magnitude of tension affects characteristics such as the maximal anterior translation or subluxation of the joint. In one study, it was found that a higher graft pretension significantly reduced postoperative anterior-posterior knee laxity. However, optimal tensioning of the reconstructed ligament may be related to graft stiffness, and different ligament reconstruction systems and graft tissue types create different stiffness values. Additionally, the optimal graft tension for men and women may be different. According to a second study, too high of an initial tension may increase the anterior-posterior knee laxity in women though the specific effects of differing graft tensions between genders is unknown. Further research in this area may find an optimal pretension value for each sex.

The tendons of the Gracilis and Semitendinosus muscles are commonly harvested for use in ACL reconstruction. The tendons are doubled over to create a four strand graft complex. During ACL reconstruction the strands are sutured to form a paired complex of either of two strands sutured together. The strength and stiffness of the graft complex typically surpass that of the native ACL, and both characteristics are optimized when a relatively even tension is applied to each of the four tendon strands.

The ConMed™ Linvatec Stress Equalization (SE™) Graft Tensioning System is a soft tissue graft tensioning system with the ability to apply different tensions to either of two sides of a graft in order to equalize stress in grafts of non-uniform diameter. The system requires multiple accessories and additional drill holes to fixate the system within the bone so that tension can be established.

The DePuy Mitek Tie Tensioner is a soft tissue graft tensioning device that requires the user to manually apply and maintain a force distal to the patient. Even tension can be achieved with this device, but requires that the suture ends be tied together to form two loops of equal length. Furthermore, limitations in the range of motion of the device's swiveling suture slide can prohibit true equality in graft strand tension. The Bio-INTRAFIX Surgical Technique manual specifies that the Tie Tensioner be used to manually apply a force of approximately 40 lbs. to the sutures while the knee is cycled to eliminate graft creep. This level of exertion often requires an additional assistant to pull the Tie Tensioner while the knee is cycled. After cycling the knee, the surgeon must maintain a force of at least 10 lbs. while the Intrafix sheath is inserted and screwed into place. Furthermore, the sheath must usually be hammered into place while tension is maintained, often requiring the assistance of an additional technician.

SUMMARY OF THE INVENTION

The inventive device is an adjustable, standalone tensioning system that requires no additional fixturing, weights, or bone surface modification, and allows a single operator to provide an adjustable and repeatable tension to a soft tissue graft, and to install the final fixation implant. Its design facilitates introduction of the suture component of the graft into the tensioning process by simplifying retention of the suture. An even, regulated and reproducible tension is easily achieved without requiring the user to manually pull on the suture strands to maintain graft tension. Furthermore, the benefits of the device's suture management system, coupled with its ability to maintain tension on the graft, minimizes obstructions surrounding the installation site and eases installation of the final fixation implant. Therefore, most surgeons will be able to use the device without requiring additional assistance during the tensioning and final fixation procedure.

The present invention is a device that is easy to use, requires no additional accessories, uses only one drill hole, and can be implanted by one practitioner. A primary goal of the inventive system and methods is to provide a means of applying a repeatable, selectable graft tension without causing additional patient trauma and to minimize the number of steps and time required to complete the soft tissue graft fixation. The device requires fewer steps and less time to operate than current state-of-the-art devices in use.

Another primary goal of the inventive device is to minimize the probability that an additional assistant be required to complete the fixation of the soft tissue graft. The device is designed so that a high initial tension can be used by a single operator to cycle the knee and eliminate graft creep, then released and reset to another value if desired for final fixation.

More particularly, in one aspect of the invention, there is provided a suture management device for use during an orthopedic procedure, which comprises a body. The device body has structure for accommodating a length of suture and a surface for engaging a portion of a patient's body for stabilizing the suture management device relative to a procedural site within the patient's body. Additionally, the body comprises a suture tensioning spring and a suture tensioning control, preferably a rotatable knob, engaged with the suture tensioning spring, for retracting the length of suture to place soft tissue to which the suture is attached in tension.

The suture management device as described above preferably further comprises a force level indicator for assisting an operator in setting a desired tensioning level. A stop is provided for limiting a distance through which the suture may be retracted, in order to limit tension imposed on the suture to a desired amount. A channel disposed in the body is provided for accommodating a tool for performing steps of the orthopedic procedure.

In one embodiment of the invention, the above mentioned surface comprises an outer surface of the body. The body comprises a center portion for channeling the length of suture between the soft tissue to be tensioned and the suture tensioning control. The body further comprises a first tensioning apparatus connected to the center portion and extending in a first direction, and a second tensioning apparatus connected to the center portion and extending in a second opposed direction. The first tensioning apparatus includes the above noted suture tensioning spring and suture tensioning control, and the second tensioning apparatus includes a second suture tensioning spring and a second suture tensioning control. The center body portion preferably comprises a curved surface and a pair of posts for retaining the suture in the center body portion.

Preferably, each of the first tensioning apparatus and the second tensioning apparatus further comprise a sliding suture cleat for receiving an end of a suture length opposed to the end connected to the soft tissue to be tensioned, wherein the sliding suture cleat slides responsive to actuation of the suture tensioning control.

In another embodiment of the invention, the surface is disposed on a force displacement arm which extends distally of the body. A force displacement tube is connected to a proximal end of the force displacement arm. A proximal end of the force displacement tube engages the suture tensioning spring. The device further comprises a rotatable suture spool for accommodating a portion of the length of suture as the suture is retracted by the suture tensioning control.

In another aspect of the invention, there is disclosed a method of tensioning a portion of soft tissue during an orthopedic procedure at an operative site in a patient's body. The disclosed method comprises steps of positioning a body of a suture management device at a desired location in proximity to the operative site, and attaching a first end of a length of suture to a portion of soft tissue to be tensioned, wherein the second end of said length of suture is attached to a suture retaining member disposed within the suture management device body. A suture tensioning control is actuated to retract the length of suture into the body, thereby tensioning the portion of soft tissue, and the tension applied to the portion of soft tissue is limited to a desired level.

In one variant of the method, the tension limiting step is performed by pre-setting a tension level using a tension adjusting control on the device. In another method variant, the tension limiting step is performed by actuating the suture tensioning control until a force gauge indicates that the desired tension level has been applied.

The method disclosed above comprises an additional step of inserting a tool through a channel in the body to deploy an implant. Then, the device is removed from the patient's body.

The invention, together with additional features and advantages thereof, may best be understood by reference to the following description taken in conjunction with the accompanying illustrative drawing.

BRIEF DESCRIPTION OF THE DRAWINGS

FIG. 3A is a view from one side of the device of FIGS. 1 and 2;

FIG. 3B is a view of the device of FIG. 3A from an orientation 90 degrees rotated from that of FIG. 3A;

FIG. 3C is a view from one end of the device of FIG. 3A;

FIG. 3D is a view from the opposed end of the device of FIG. 3A;

FIG. 6 is an exploded view of the suture tensioning device of FIG. 5;

FIG. 7 is a detailed view of the portion of FIG. 6 which is delineated by circle 7.

DESCRIPTION OF THE PREFERRED EMBODIMENT

Figure 1A:
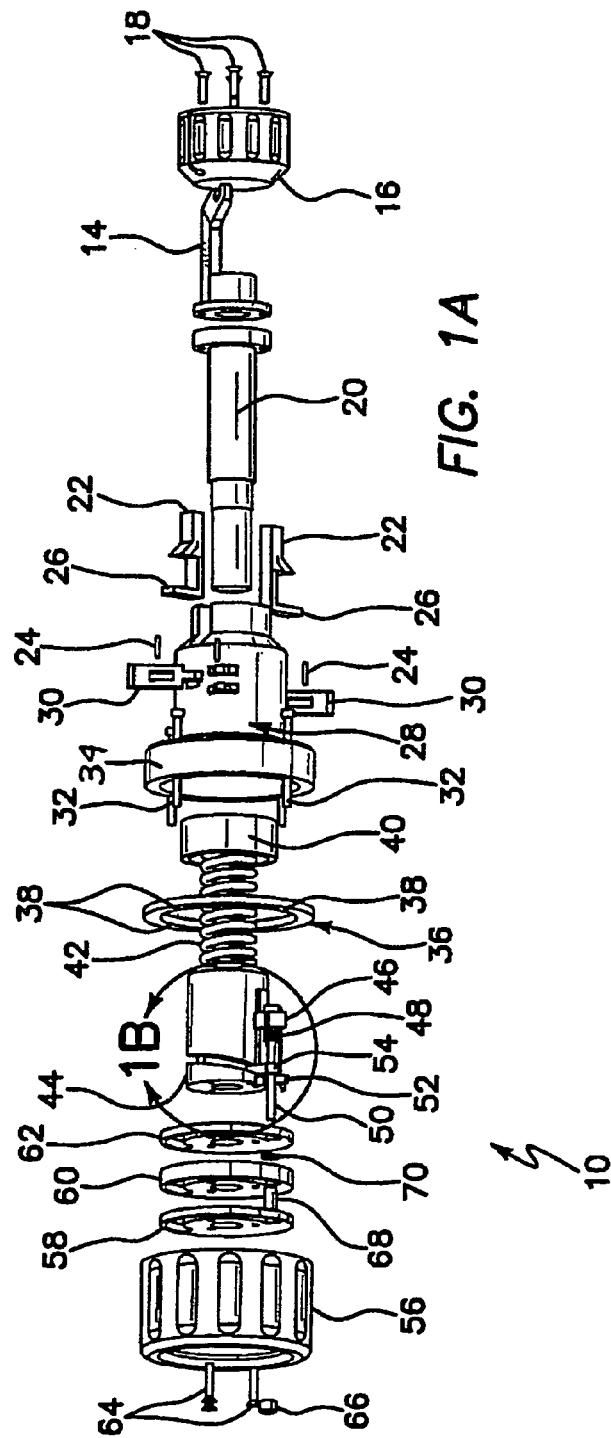
FIG. 1A is an isometric exploded view of an embodiment of a device constructed in accordance with the principles of the present invention.
Figure 1B:
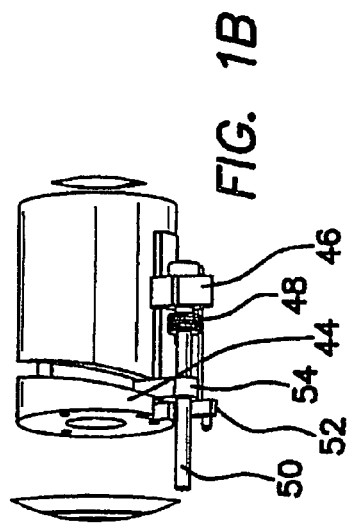
FIG. 1B is a detailed view of the portion of FIG. 1A delineated by circle 1B.
Figure 2:
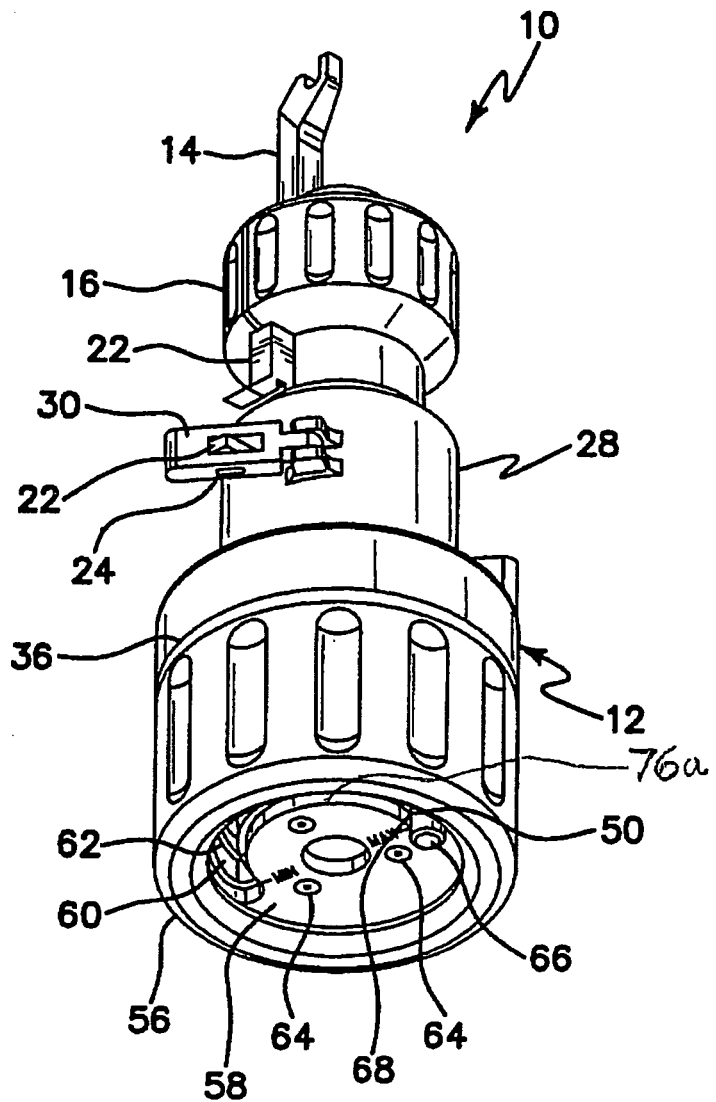
FIG. 2 is an isometric view of the assembled device of FIG. 1A.

Referring now more particularly to the drawings, there is shown in FIGS. 1-3 a suture tensioning device 10 comprised of a body 12. The device 10 comprises a force displacement arm 14, which functions to fix the device 10 against the wall of a tibial tunnel 15 (FIG. 4A), as will be described hereinbelow. The force displacement arm 14 is shaped to flexibly accommodate different topographies with acceptable clearance for both the final fixation implant and any installation tools. With slight modification of the design, the force displacement arm 14 may be made removable and replaceable so that the tensioning device 10 can be either a single use device or reusable.

Proximal to the force displacement arm 14 is a suture guide knob 16. Fasteners 18 (FIG. 1A) secure the force displacement arm 14 to a force displacement tube 20 within the suture guide knob 16. The device 10 further comprises a plurality of suture drawers 22. Pins 24 are adapted for insertion through pin apertures 26 in the suture drawers 22. A rotatable suture spool 28 is provided, on which are disposed a plurality of thumb levers 30.

Fasteners 32 extend through a flange 34 on the rotatable suture spool 28, for attaching the flange 34 to a ratchet gear 36, through apertures 38. A spring collar stop 40 and a tensioner spring 42 are disposed within the rotatable suture spool 28, as shown in FIG. 1A. Slidable about a proximal end of the tensioner spring 42 is a spring collar slide 44. A pawl 46 and a ratchet torsion spring 48 are provided, wherein the ratchet torsion spring 48 is disposed about an adjustment slide rod 50. An adjustment lock 52 and a sliding stop 54 are also provided, as shown.

At a proximal end of the device 10, there is provided a tensioning knob 56. Within the tensioning knob 56 are disposed, in cooperating relationship, an adjustment cover 58, a washer retainer 60, and a gauged cover plate 62. Fasteners 64 assist in securing the adjustment cover 58, washer retainer 60, and gauged cover plate 62 within the tensioning knob 56. A tension adjust button 66 extends proximally from the adjustment cover, and is connected to an adjustment spring 68 and a spring support washer 70, which, in turn, are operatively disposed on a proximal end of the adjustment slide rod 50.

Figures 4A, 4B:
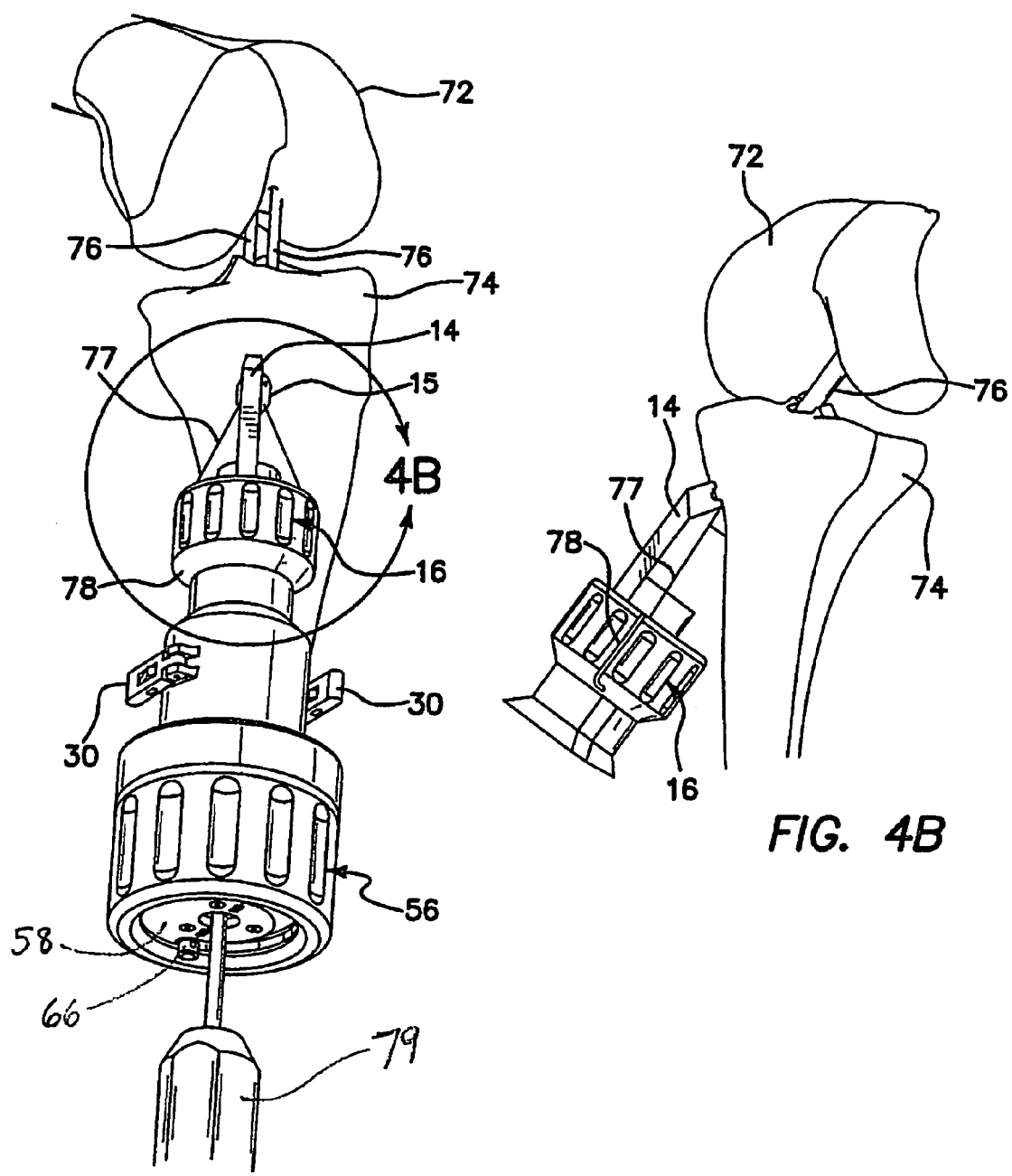
FIG. 4A is an isometric view illustrating a clinical application of the device of FIGS. 1-3.
FIG. 4B is a detailed view of the portion of FIG. 4A delineated by the circle B, taken from the side.
Figure 5:
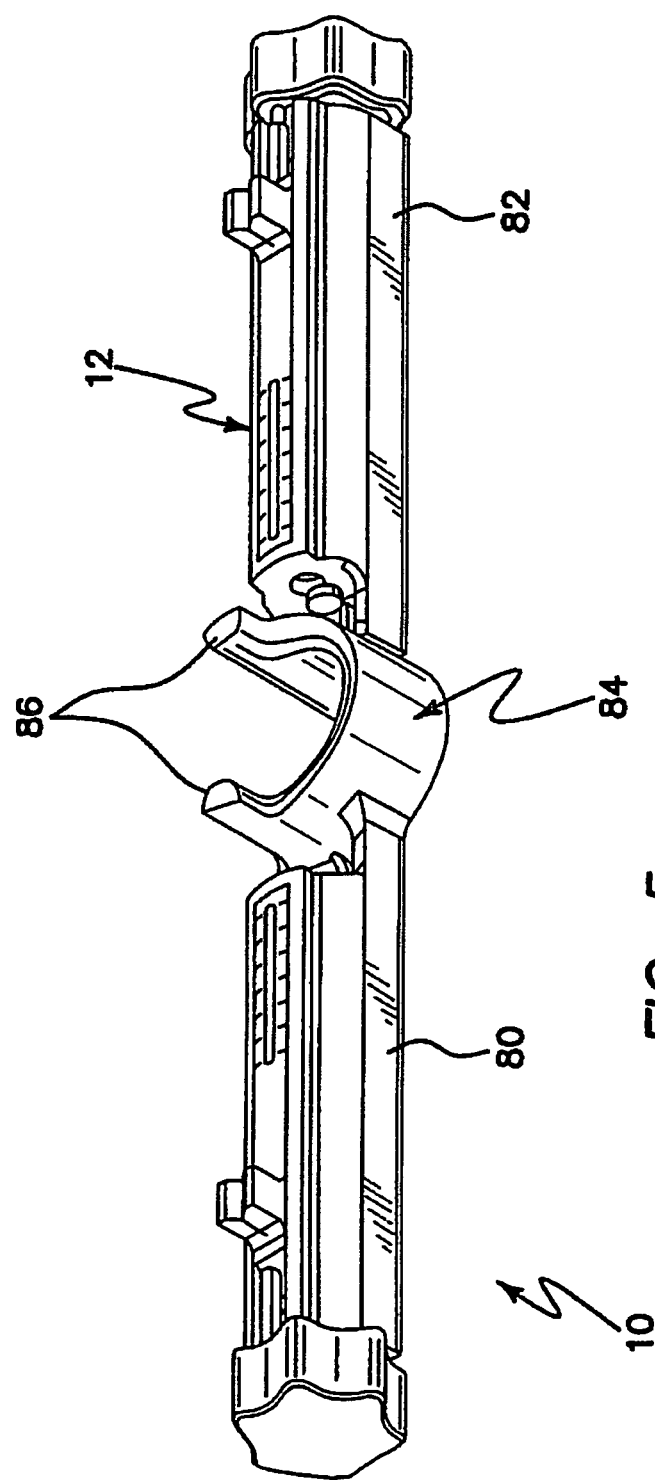
FIG. 5 is a perspective view of a modified embodiment of the suture tensioning device of the present invention.
Figure 8:
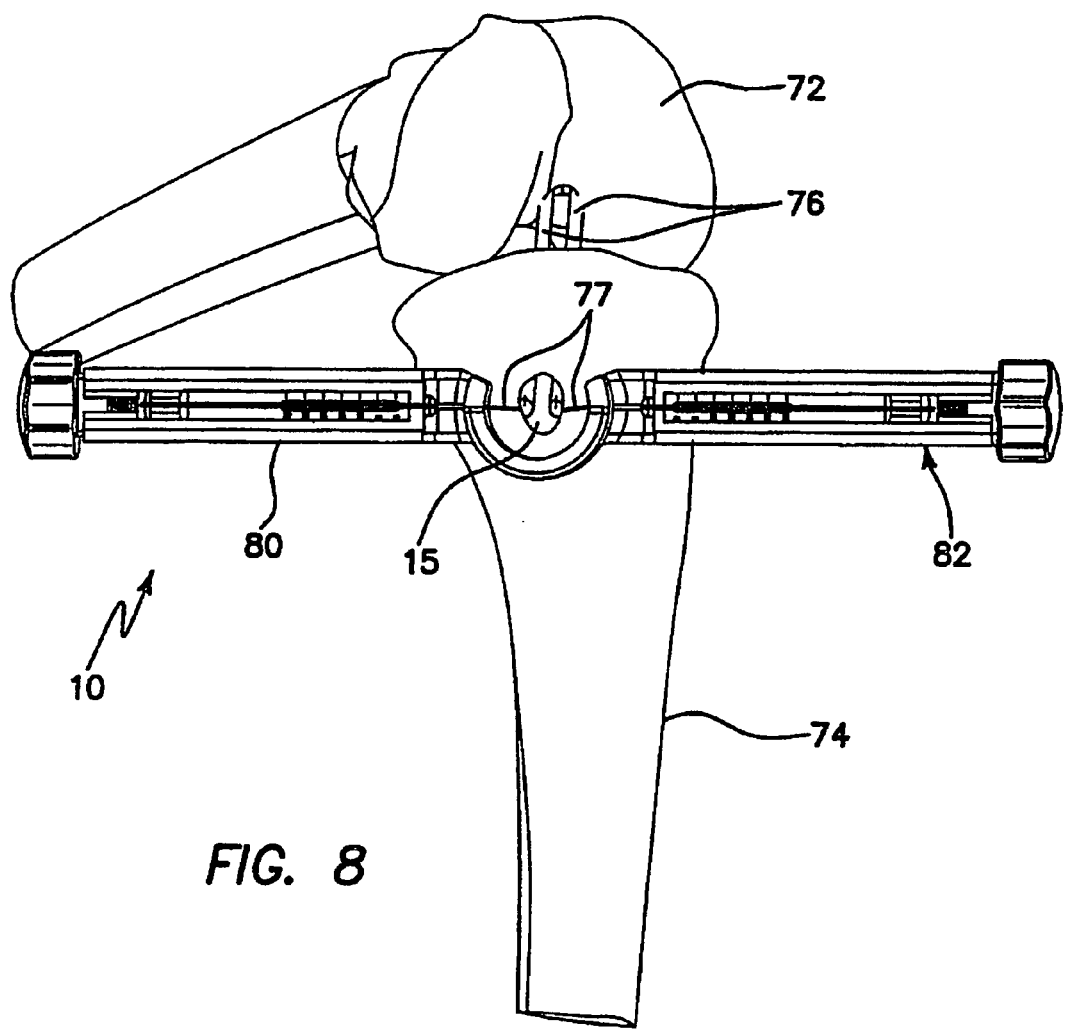
FIG. 8 is a view illustrating a clinical application of the device of FIG. 5.

Now with reference to FIGS. 4A and 4B, a method for using the device 10 will be described. In this particular example, the suture tensioning device 10 is used in the performance of an ACL repair, of the types disclosed in U.S. Patent Application Publication No. 2006/0155287, entitled Devices, Systems, and Methods for Material Fixation, in U.S.

patent application Ser. No. 11/725,981, entitled Devices, Systems, and Methods for Material Fixation, filed on Mar. 20, 2007, and in U.S. patent application Ser. No. 11/923,526, entitled Methods & Systems for Material Fixation, filed on Oct. 24, 2007. All of these prior applications are commonly assigned with the present application, and are herein expressly incorporated by reference, in their entirety. This particular procedure is exemplary only, as the device 10 and methods of the present invention may be used in a variety of procedures during which it is necessary or desirable to tension portions of the tissue.

Illustrated are the femur 72 and tibia 74 of a patient. As graft tendons 76 are pulled proximally and become tensioned, displacement is constrained by the design to occur at the force displacement arm 14, whose load is transferred to the force displacement tube 20, spring collar stop 40, and tensioner spring 42. The displacement of these components is adjustably limited by the sliding stop 54. This component controls the maximum displacement of the tensioner spring by preventing further displacement once it is in contact with the spring collar stop 40. The tensioner spring 42 is housed within the spring collar slide 44 and is so constrained. The tensile force imposed on the tendons 76 can be estimated by multiplying the tensioner spring constant by the displacement distance traveled by the tensioner spring 42.

Known values of force or a qualitative scale can be marked on the adjustment cover 58 or the force displacement tube 20. The position of the tension adjust button 66 indicates the tension setting and relates the circumferential position of the sliding stop 54 to a displacement tangential along the spring collar slide 44. The tensioning device is adjusted by depressing the tension adjust button 66 and sliding it to the desired tension force marked on the adjustment cover 58. The tension adjust button 66, adjustment spring 68, spring support washer 70, and adjustment slide rod 50 slide along an aligned track 76a (FIG. 2) formed by the adjustment cover 58, washer retainer 60, and gauged cover plate 62. Depressing the tension adjust button 66 compresses the adjustment spring 68, lowers the adjustment slide rod 50, and thus disengages the adjustment lock 52 from a mated hole on the perimeter of the gauged cover plate 62 corresponding to a specific tension setting. Consequently, the pawl 46 disengages from the ratchet gear 36. As the adjustment slide rod 50 moves circumferentially around the aligned track formed by the adjustment cover 58, the washer retainer 60, and the gauged cover plate 62, it rotates the sliding stop 54 around the perimeter of the spring collar slide 44. A spiral shaped cut translates circumferential movement of the sliding stop 54 into a tangential motion along the length of the spring collar slide 44, thereby adjustably limiting the maximum possible displacement for the force displacement arm 14, force displacement tube 20, spring collar stop 40, and thus the tensioner spring 42.

Once the desired tension is set, the tension adjust button 66 is released, allowing the adjustment spring 68 to return the adjustment slide rod 50 and to re-engage the adjustment lock 52 into a mated hole of the gauged cover plate 62, which corresponds to the desired tension setting. Simultaneously, the pawl 46 re-engages with the ratchet gear 36 assisted by the angle-chamfered teeth of the lower half of the ratchet gear 36.

Once the force displacement arm 14 is properly positioned, after the desired tension is set, suture 77 can be loaded into the suture drawers 22. Optionally, the device may be packaged with the suture drawers in a state ready for loading, and in this configuration, any potential displacement of the force displacement arm 14 is prohibited by the interference created between lower portions of the suture drawers 22 and the suture guide knob 16. Two or more suture drawers 22 contain a suture slot feature which can accommodate multiple strands of a plurality of suture sizes. Moreover, the suture guide knob 16 also contains two or more suture slot features 78 (FIG. 4B) which provide channels for the suture strands to be guided within and removed from hindrance. Thumb levers 30 are attached to the rotatable suture spool 28 by pins 24. Slots in the thumb levers 30 allow movement of the pin 24 press fit through the suture drawer 22. When the thumb lever 30 is depressed inwardly toward the rotatable suture spool 28, the suture drawers 22 retract into a cavity within the rotatable suture spool 28. The width of the suture drawers 22 steps down at the location of the suture slots 78 to accommodate the width of the suture as it retracts into the cavity. Once the suture drawers 22 are retracted, the interference between the cavity walls of the rotatable suture spool 28, the suture strands, and the suture drawers constrains the suture strands 77 from moving.

When the suture strands 77 of approximately equal length have been passed through the suture guide knob 16, after the desired tension level has been set, and loaded into the suture drawers 22, the device is ready to tension the suture strands and soft tissue graft, to which the suture strands are connected. The operator simply grasps the suture guide knob 16 with one hand while rotating the tensioning knob 56 in a clockwise motion with the other hand. During the tensioning process, the device is held parallel to the graft tunnel. The tensioning knob 56 is rotated until it stops. At this point, the desired tension has been reached and the sliding stop 54 has come into contact with the spring collar stop 40, thereby prohibiting further displacement of the tensioner spring 42. Tension is achieved as the suture strands 77, whose ends are constrained within the suture drawers 22, wrap and accumulate around the rotatable suture spool 28. The load propagates along the suture strands, equally tensioning each strand of the soft tissue graft 76.

The tensioning knob 56 rotates the ratchet gear 36 and the rotatable suture spool 28. The inner components of the device are prevented from rotating as they are fixed in relation to the suture guide knob 16. A keyway internal to the spring collar slide 44 and the spring collar stop 40 prohibits rotation of the spring collar slide 44 and its attached components. The pawl 46 is therefore fixed in place relative to the suture guide knob 16. As the ratchet gear 36 rotates clockwise around the inner components, the pawl 46 alternately moves in a clicking fashion along and opposite to the tangential vector of ratchet gear rotation. The ratchet torsion spring 48 returns the pawl 46 to its original position between the teeth of the ratchet gear 36. Motion of the tensioning knob 56 is restricted to the clockwise direction by a feature on the side of the pawl 46 that interferes with one edge of the sliding stop 54. If motion is attempted in the counter-clockwise direction, the pawl 46 is obstructed from moving by the sliding stop 54 and the ratchet gear 36 is prevented from rotating. The ratcheting mechanism of this device is not limited to the description provided herein, but may also constitute similarly functional configurations utilizing a variety or a plurality of pawls, gears, teeth or grooves. it is also within the scope of the present invention to utilize a one-way (Sprag freewheel type) rotational bearing in place of the above described ratcheting mechanism.

If used during the course of a ligament reconstruction procedure, such as that described in co-pending U.S. application Ser. No. 11/725,981, already expressly incorporated by reference herein, the soft tissue graft is first located in a tunnel drilled through the tibia, and a femoral anchor is deployed to secure a distal end of the graft in a socket drilled into the femur. Then, the proximal end of the soft tissue graft is extended proximally through the tibial tunnel and through receiving portions of a tibial anchor. Before the tibial anchor is deployed, the graft is tensioned by pulling it taut, using the device 10. After tensioning of the soft tissue graft has been completed, the device can be held with one hand while the joint (knee) is cycled to eliminate graft creep. Afterwards, the tension can be readjusted to a lower value for final fixation by holding the suture guide knob 16, and while disengaging the ratchet mechanism by pressing the tension adjust button 66, rotating the tensioning knob 56 counter-clockwise to unwind some or all suture from the suture spool 28. The new tension can be assessed by looking at where gauged markings on the force displacement tube 20 align with the edge of the suture guide knob 16 or by releasing all tension and repeating the tensioning procedures with the newly desired value. Once the desired final fixation tension is reached, the implant is positioned and an implant installation tool 79 is inserted and operated through the center of the tensioning device, as illustrated in FIGS. 4A and 4B. The device is removed from patient contact by either cutting the suture strands, thus separating the device 10 from the soft tissue grafts, or by opening the suture drawers 22 using the thumb levers 30.

A second, modified embodiment of the device of the present invention is illustrated in FIGS. 5-8. In this embodiment, like elements to those illustrated in FIGS. 1-4 are delineated by like reference numerals. The embodiment of FIG. 5 differs from the FIG. 1 embodiment in that the tendon bundles 76 are tensioned laterally to the tibial tunnel 15 (FIG. 8) rather than axially. Instead of pushing off of a cortical bone surface, the device 10 of FIG. 5 rests on the surrounding bone and/or tissue during the tensioning procedure. The device 10 comprises two tensioning assemblies 80, 82 that are symmetric about the center of the tensioner body 12. A center portion 84 of the tensioner body 12 is filleted with a large radius to provide a smooth transition for the tensile force to translate around the bend of the suture strands to the tendon bundles within the tibial tunnel. The C-shaped center portion 84 of the tensioner body 12 is left open, allowing the suture strands 77 (FIG. 8) to be passed over the filleted edges of the center portion of the tensioner body 12 rather than being threaded through an otherwise closed portion. The open center portion 84 also facilitates implant insertion and installation. The tibial tunnel 15 (FIG. 8) is angled with respect to the surface of the knee (tibia 74), so the inclusion of two posts 86 at the edges of the C-shaped center portion 84 of the tensioner body 12 prevents the sutures 77 from sliding off of the edge of the tensioner body during the tensioning procedure.

The patient contact side of the tensioner body 12 has two sliding suture cleats 88 (FIGS. 6 and 7) located at each end of the device, that fixate the suture strands of the soft tissue graft for tensioning. Each tensioning knob 56 is fixed to a force translation screw 90. When the knob is rotated, a threaded force translation nut 92 moves linearly along the length of the tensioner body 12. The tensioning nut 92 is prevented from rotating relative to the tensioner body 12 by the extruded portion of the nut that slides within a channel on the top surface of the tensioner body 12.

The tensioning knob 56 and force translation screw 90 are constrained within the cylindrical cavity of the tensioner body by the outside diameter of the tensioning knob shaft, which lies partly inside the slightly larger inner diameter of the tensioner body, allowing for rotation of the tensioning knob 56. The end of the force translation screw 90 opposite to the tensioning knob 56 has a notch machined into it so that it can be installed through a keyhole snap within the tensioner body 12. The keyhole snap retains the opposite end of the force translation screw and allows only rotational movement of the screw.

As the tensioning knob 56 is rotated in the appropriate direction, the force translation nut 92 moves away from the center of the tensioner body and begins to compress the tensioning spring 42, which is press fit over the force translation nut 92 and sliding suture cleat 88, maintaining the motion of the force translation nut and the sliding suture cleat relative to one another. Each end of the tensioning assembly is designed to remove any slack from the tendon bundles and suture strands by the allowance for a displacement distance beyond the combined length of the assembly of the tensioning spring 42, force translation nut 92, and sliding suture cleat 88. Rotating the tensioning knob 56 will remove any slack in the tendon bundles within this allowance prior to establishing tension.

The tensioning spring 42 directs the compressive force created by the linear displacement of the translation nut to the sliding suture cleat 88 which is constrained from movement by the cleated suture strands leading into the tibial tunnel. Each force translation screw 90 and force translation nut 92 may be threaded oppositely to one another, allowing the force translation nuts 92 to compress the tensioning springs 42 while rotating the tensioning knobs 56 in the same direction, instead of in opposing directions. An indicator pin or other marking on the force translation nut 92 moves either underneath or relative to a slot on the sliding suture cleat/force gauge 88 which may be translucent, for purposes of reading the force indicator mark of the force translation nut 92 if the post and slot configuration is not used.

The sliding suture cleat/force gauge 88 has linear gradient markings which relate displacement of the tensioning spring 42 to force in either lbf or N. A typical tensioning range for each tendon bundle may be from 0 to 30 lbf (0 to 133.45 N). However, the tension on either side of the device may be set to any value within this range by rotating the tensioning knob until the desired tension is reached. The design of the device allows tension to be set and maintained without requiring the physician to physically hold the tensioning knobs. Therefore, the device can be used by a single physician without additional assistance.

The device is designed so that once tension is established, the physician can have both hands free to complete the installation of the final fixation implant. In the example cited above, involving the repair of an ACL as described in the co-pending '981 application, the final fixation implant is the tibial anchor, the femoral anchor having already been installed prior to tensioning. Similar to the ConMed Linvatec SE™ (Stress Equalization) Graft Tensioning System, the disclosed device permits the physician to independently tension each tissue graft bundle to normalize stress between bundles of differing cross-sectional area, but with fewer steps, greater ease, and less time. Moreover, the design of the tensioning device assists implant installation by separating and spreading the tendon bundles to the edges of the tibial tunnel, thus facilitating the process of inserting the tibial implant between the tendons. Once the implant is installed, the device is removed from patient contact by either cutting or unwinding the suture strands from the suture cleats.

Accordingly, although an exemplary embodiment of the invention has been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A suture management device for use during an orthopedic procedure comprising:

a first body, a center portion and a second body wherein said first body and said second body are each connected to said center portion such that the first and second bodies are symmetric about the center portion and wherein the first body extends away from the center portion longitudinally in a first direction and the second body extends away from the center portion longitudinally in a second direction directly opposed to said first direction, the center portion being C-shaped, each of the first and second bodies further comprising:

a surface disposed on the first and second bodies and structured for resting portions of a patient's body for stabilizing the suture management device relative to a procedural site within the patient's body;

a structure accommodating a length of suture; and a tensioning apparatus comprising a suture tensioning spring;

wherein the tensioning apparatuses of each of the first and second bodies are disposed, respectively, on each of the first and second bodies, so that the respective suture tensioning springs of each suture tensioning apparatus are aligned longitudinally with one another.

2. The suture management device as recited in claim 1, wherein the tensioning apparatus in said first body includes a first one of said suture tensioning springs and a first suture tensioning control engaged with said first suture tensioning spring, and the tensioning apparatus in said second body includes a second one of said suture tensioning springs and a second suture tensioning control engaged with said second suture tensioning spring, wherein each of said tensioning apparatuses are adapted for retracting the lengths of sutures to place soft tissue to which the sutures are attached in tension.

3. The suture management device as recited in claim 1, wherein said center portion comprises a curved surface and a pair of posts for retaining the sutures in the center portion.

4. The suture management device as recited in claim 2, wherein each of said tensioning apparatuses further comprises a sliding suture cleat for receiving an end of a suture length opposed to the end connected to the soft tissue to be tensioned, the sliding suture cleat sliding responsive to actuation of the suture tensioning control.

* * * * *